(12) United States Patent
Abu Osman et al.

(10) Patent No.: US 8,999,004 B2
(45) Date of Patent: Apr. 7, 2015

(54) MAGNETIC COUPLING DEVICE OF A LIMB PROSTHESIS

(71) Applicant: Universiti Malaya, Kuala Lumpur (MY)

(72) Inventors: Madya Noor Azuan Abu Osman, Kuala Lumpur (MY); Arezoo Eshraghi, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 0 days.

(21) Appl. No.: 13/865,677

(22) Filed: Apr. 18, 2013

(65) Prior Publication Data
US 2013/0289743 A1    Oct. 31, 2013

(30) Foreign Application Priority Data

Apr. 25, 2012  (MY) .......................... PI 2012700220

(51) Int. Cl.
| | | |
|---|---|---|
| A61F 2/80 | (2006.01) | |
| H01F 7/02 | (2006.01) | |
| H01H 9/00 | (2006.01) | |
| A61F 2/78 | (2006.01) | |

(52) U.S. Cl.
CPC ............... *A61F 2/7812* (2013.01); *A61F 2/78* (2013.01); *A61F 2/80* (2013.01)

(58) Field of Classification Search
CPC .............. A61F 2/60; A61F 2/78; A61F 2/80; A61F 2002/5004; A61F 2002/7868
USPC ........... 623/27–28, 30–33, 35–36, 58; 24/303
See application file for complete search history.

(56) References Cited

U.S. PATENT DOCUMENTS

| | | | | |
|---|---|---|---|---|
| 2,528,271 | A  * | 10/1950 | Gibbs et al. ................... | 242/288 |
| 4,779,314 | A  * | 10/1988 | Aoki ............................... | 24/303 |
| 6,273,918 | B1 * | 8/2001 | Yuhasz et al. .................. | 623/33 |
| 8,540,292 | B2 * | 9/2013 | Ferguson .................... | 292/251.5 |
| 2003/0079581 | A1 * | 5/2003 | Beauchamp .................... | 81/490 |
| 2010/0251574 | A1 * | 10/2010 | Battlogg et al. ............. | 36/117.1 |
| 2011/0093090 | A1 * | 4/2011 | Olafsson et al. ................ | 623/38 |

OTHER PUBLICATIONS

Jim Coleman. Below-Knee Pylon Laminating and Set-up Technique. Oct. 2008.*

\* cited by examiner

*Primary Examiner* — Thomas J Sweet
*Assistant Examiner* — Christie Bahena
(74) *Attorney, Agent, or Firm* — Suzannah K. Sundby, Esq.; Canady + Lortz LLP

(57) ABSTRACT

The present invention relates to a coupling device (100) for connecting a residual limb liner (10) to a residual limb socket (20) of a limb prosthesis, characterized by: a magnet assembly (120) comprising a permanent magnet (122) sandwiched by a pair of iron bars (124) for creating a magnetic field; a housing (110) comprising a protrusion (112) for intensifying magnetic field and a cavity (114) for receiving the magnet assembly (120), wherein said housing (110) is embedded at a distal end of the residual limb socket (20); a controlling means (130) coupled to the housing (110) and the magnet assembly (120) for controlling the magnetic field by rotating the magnet assembly (120); and a mounting plate (140) coupled to the residual limb liner (10); wherein the mounting plate (140) is attracted to the protrusion (112) of the housing (110) when the permanent magnet (122) is vertically aligned, thereby attaching the residual limb liner (10) to the residual limb socket (20); and wherein the mounting plate (140) is repelled from the protrusion (112) of the housing (110) when the permanent magnet (122) is horizontally aligned, thereby detaching the residual limb liner (10) from the residual limb socket (20).

6 Claims, 3 Drawing Sheets

MAGNETIC COUPLING DEVICE OF A LIMB PROSTHESIS

BACKGROUND OF THE INVENTION

1. Field of the Invention

This invention relates to a coupling device for a limb prosthesis, and more particularly to a magnetic coupling device for connecting a residual limb liner to a residual limb socket of a limb prosthesis, which is applicable for lower limb prosthesis as well as for upper limb prosthesis.

2. Description of Related Arts

Lower limb prosthetics are artificial devices designed to replace the function or appearance of all or a part of the missing lower limb. In contrast, lower limb orthotic devices are designed to support, supplement, or augment the function of an existing lower limb.

All types of lower limb prosthesis include a foot and socket. The socket is part of the prosthesis that connects to the stump. The stump is the end of the lower limb. A pylon is a tube connecting the socket to the foot. A pylon may be used to transfer body weight from the socket to the foot. A suspension system or a coupling system is required for a limb prosthesis to suspend a prosthetic limb from a residual limb for extending to the ground to provide body support, to prevent prosthesis from falling off, as well as to avoid pistoning, and to minimize shear forces on the skin of the amputation limb.

There are various suspension systems or coupling devices that are available in the industry. For instance, a shuttle lock which provides rigid attachment of the liner to the socket and lower leg components, or a suction suspension liner with hypobaric sealing membrane around the silicone liner without an external sleeve or shuttle lock to increase surface contact with the socket wall.

Some of the suspension systems in prior arts utilise suction by venting air from between the residual limb and the socket part during insertion of the limb and is prevented from re-entering through the socket part to maintain the vacuum. For instance, disclosed in U.S. Pat. No. 7,947,085 B2 is a prosthetic device utilizing electric vacuum pump for evacuating the socket of a prosthetic limb, and prosthetic limb system employing such vacuum devices. The prosthetic device comprises a prosthetic socket adapted to receive a residual limb, a vacuum passageway through said prosthetic socket, and an evacuation device comprising an electrically powered vacuum pump and a source of electric power.

Another prior art relates to a suspension/alignment for prosthetic limbs is disclosed in U.S. Pat. No. 6,063,125. Said prosthetic limb suspension system relates to a distal adaptor incorporating an air valve, or a simplified distal adaptor for use with thermoplastic sockets. Also disclosed in U.S. Pat. No. 6,267,787 is a prosthetic attachment locking assembly having prosthetic attachment lock which locks a residual limb stump to a prosthetic limb. Another similar art disclosed in U.S. Pat. No. 7,083,654 is a prosthetic angled locking coupler device for connecting a residual limb socket to a lower limb prosthesis.

The existing systems, however, suffer from a number of shortcomings. One is that the system may result in distal tissue stretching, and pistoning of the prosthesis. This can cause permanent elongation of distal tissue and augment pistoning. Furthermore, the use of the systems may lead to pain, particularly along the tibial crest and cut end of the tibia among transtibial amputees and cut end of the femur among transfemoral amputees. Some patients may experience problem when aligning pin with the plunger pin hole or disengaging pin from the pin lock, particularly to the patients with poor flexibility, strength, and/or manual dexterity, thus causing difficulty and dissatisfaction among the amputees, and raise the problem of aligning and adjusting the liner to the socket.

Also, the complex design of the suspension system renders high cost and time consumption, as well as system failure or improper function due to the accumulation of dust, dirt and other debris within the system. In addition, the donning and doffing problems may arise if the configuration of the systems is complicated.

Accordingly, it can be seen in the prior arts that there exists a need to provide a coupling device for connecting a residual limb liner to a residual limb socket of a limb prosthesis which is simple and easy to be used by amputees, as well as to provide a system to overcome the existing problems.

SUMMARY OF INVENTION

It is an objective of the present invention to provide a coupling device for connecting a residual limb liner to a residual limb socket of a limb prosthesis.

It is also an objective of the present invention to provide a magnetic coupling device of a limb prosthesis that is attachable and detachable from a residual limb socket by switching the magnetic field.

It is yet another objective of the present invention to provide a coupling device of a limb prosthesis that is embedded within the residual limb socket for eliminating donning and doffing problems.

It is a further objective of the present invention to provide a coupling device of a limb prosthesis that is simple and user-friendly to facilitate and to ease the use by amputees.

Accordingly, these objectives may be achieved by following the teachings of the present invention. The present invention relates to a coupling device for connecting a residual limb liner to a residual limb socket of a limb prosthesis, characterised by: a magnet assembly comprising a permanent magnet sandwiched by a pair of iron bars for creating a magnetic field; a housing comprising a protrusion for intensifying magnetic field and a cavity for receiving the magnet assembly, wherein said housing is embedded at a distal end of the residual limb socket; a controlling means coupled to the housing and the magnet assembly for controlling the magnetic field by rotating the magnet assembly; and a mounting plate coupled to the residual limb liner; wherein the mounting plate is attracted to the protrusion of the housing when the permanent magnet is vertically aligned, thereby attaching the residual limb liner to the residual limb socket; and wherein the mounting plate is repelled from the protrusion of the housing when the permanent magnet is horizontally aligned, thereby detaching the residual limb liner from the residual limb socket.

BRIEF DESCRIPTION OF THE DRAWINGS

The features of the invention will be more readily understood and appreciated from the following detailed description when read in conjunction with the accompanying drawings of the preferred embodiment of the present invention, in which.

DETAILED DESCRIPTION OF THE INVENTION

Figure 1:
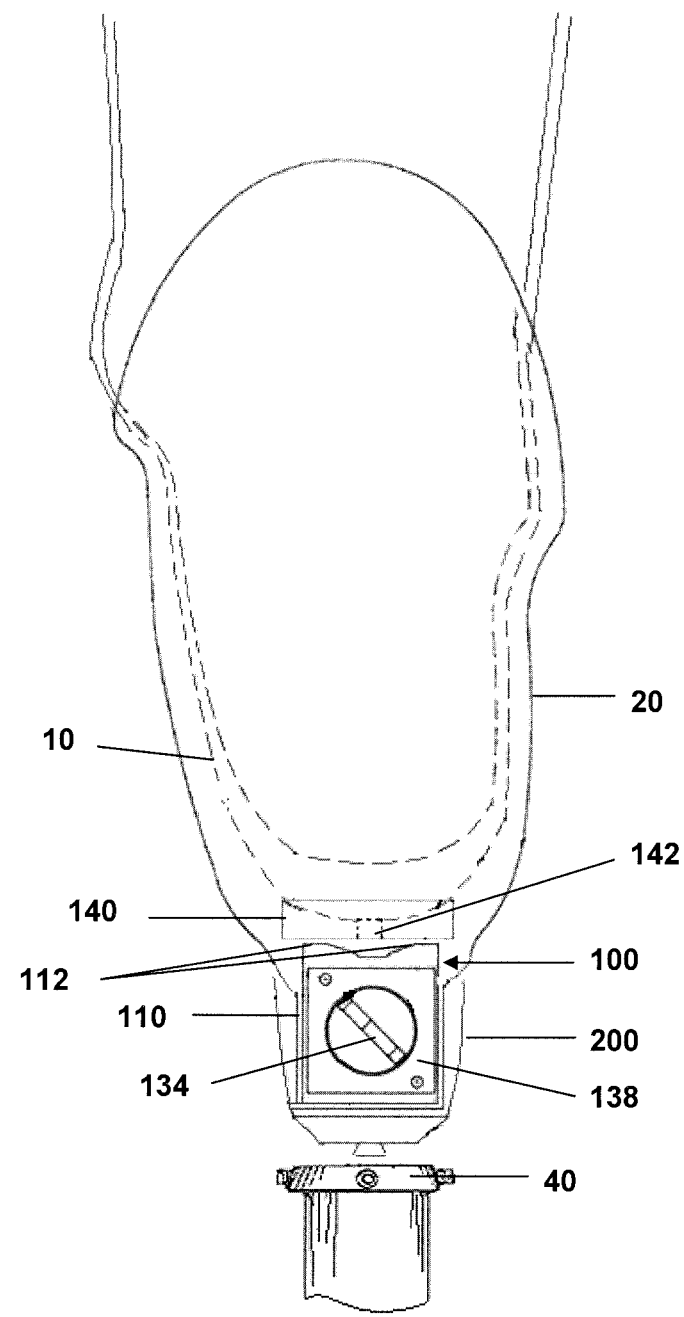
FIG. 1 is a lateral view of an assembled coupling device embedded at a distal end of a residual limb socket of a limb prosthesis.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all modification, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations or technical terms are used, these indicate the commonly accepted meanings as known in the technical field. For ease of reference, common reference numerals will be used throughout the figures when referring to the same or similar features common to the figures. The present invention will now be described with reference to FIGS. 1-4b.

The present invention relates to a coupling device (100) for connecting a residual limb liner (10) to a residual limb socket (20) of a limb prosthesis by utilizing magnetic field. Said coupling device (100) is applicable for upper limb prosthesis as well as for lower limb prosthesis.

Said coupling device (100) for connecting a residual limb liner (10) to a residual limb socket (20) of a limb prosthesis, characterised by:
- a magnet assembly (120) comprising a permanent magnet (122) sandwiched by a pair of iron bars (124) for creating a magnetic field;
- a housing (110) comprising a protrusion (112) for intensifying magnetic field and a cavity (114) for receiving the magnet assembly (120), wherein said housing (110) is embedded at a distal end of the residual limb socket (20);
- a controlling means (130) coupled to the housing (110) and the magnet assembly (120) for controlling the magnetic field by rotating the magnet assembly (120); and
- a mounting plate (140) coupled to the residual limb liner (10);

wherein the mounting plate (140) is attracted to the protrusion (112) of the housing (110) when the permanent magnet (122) is vertically aligned, thereby attaching the residual limb liner (10) to the residual limb socket (20); and wherein the mounting plate (140) is repelled from the protrusion (112) of the housing (110) when the permanent magnet (122) is horizontally aligned, thereby detaching the residual limb liner (10) from the residual limb socket (20).

In a preferred embodiment of the coupling device (100), the controlling means (130) comprises: a pair of covers (132) coupled to two ends of the magnet assembly (120) to facilitate the rotation of the magnet assembly (120), a knob (134) attached to one of the covers (132) at an outer end of the magnet assembly (120), with a washer (136) placed therebetween, for controlling the rotation of the magnet assembly (120), and a frame (138) coupled to the knob (134) and fastened to the housing (110) to locate the knob (134).

In a preferred embodiment of the coupling device (100), the housing (110) is mounted on a pylon (40) of a limb prosthesis by fastening means.

In a preferred embodiment of the coupling device (100), the mounting plate (140) is made of stainless steel.

In a preferred embodiment of the coupling device (100), the mounting plate (140) has a flat surface for distributing the magnetic field evenly on said plate (140).

In a preferred embodiment of the coupling device (100), the mounting plate (140) is provided with a male connector (142) adapted to be received in a female connector located on a distal end of the residual limb liner (10), for fastening the mounting plate (140) to the residual limb liner (10).

Referring to FIG. 1, the coupling device (100) is attached to the distal end of the residual limb socket (20). The coupling device (100) is preferably embedded within the residual limb socket (20) at the distal end to enable the attachment of the residual limb liner (10) to the residual limb socket (20). The residual limb socket (20) may include a cup-shaped component (200) extending from the distal end of the residual limb socket (20) to accommodate the coupling device (100) within the socket (20). Said coupling device (100) may be fastened to the cup-shaped component (200) by any fastening means including a screw, an adhesive and the like. Said cup-shaped component (200) may extend downwardly and couple to the pylon (40) using any fastening means, for instance, a 3-prong-adapter. The coupling device (100) may be disposed at an outer side of the limb prosthesis to ease the switching of the controlling means (130) by a user. The mounting plate (140) is disposed within the residual limb socket (20) on top of the housing (110) and coupled to the distal end of the residual limb liner (10).

Figure 2:
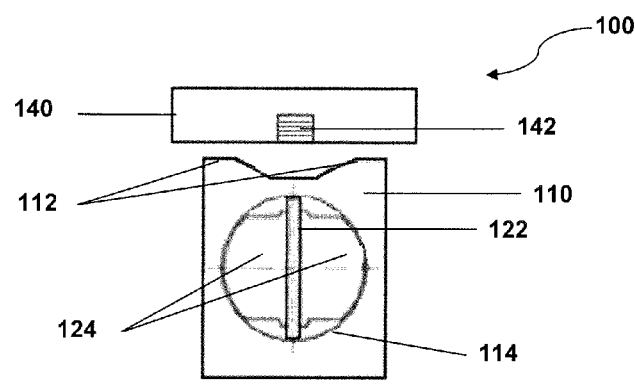
FIG. 2 is a cross-sectional view showing a partial assembled coupling device of the present invention.

FIG. 2 shows a partial assembled coupling device (100) which comprises the magnet assembly (120) including the permanent magnet (122) located between the pair of iron bars (124), the housing (110) having the protrusion (112) on top of the housing (110) and the cavity (114) for receiving the magnet assembly (120), and the mounting plate (140) located on top of the housing (110). The controlling means (130) coupled to the housing (110) and the magnet assembly (120) are shown in FIG. 3.

As shown in FIG. 2, the mounting plate (140) preferably has a flat bottom surface for distributing the magnetic field of the magnet assembly (120) evenly on said mounting plate (140). Also, the flat surface of the mounting plate (140) helps to distribute the user's body weight evenly on the limb prosthesis and increase the contact surface between the mounting plate (140) and the housing (110). The increased contact surface thus eliminates the problem of distal tissue stretching and the resultant pain. The mounting plate (140) is preferably provided with the male connector (142) extending from the bottom of the plate (140). The male connector (142) is adapted to be received in the female connector located on the distal end of the residual limb liner (10), as can be seen in FIG. 1. The male connector (142) is preferably a threaded stud that is screwed into the female connector. The mounting plate (140) may be made of any material that is attracted to the magnet assembly (120). In the preferred embodiment, the mounting plate (140) is made of stainless steel having anti-corrosion properties and has a longer life-span.

Figure 3:
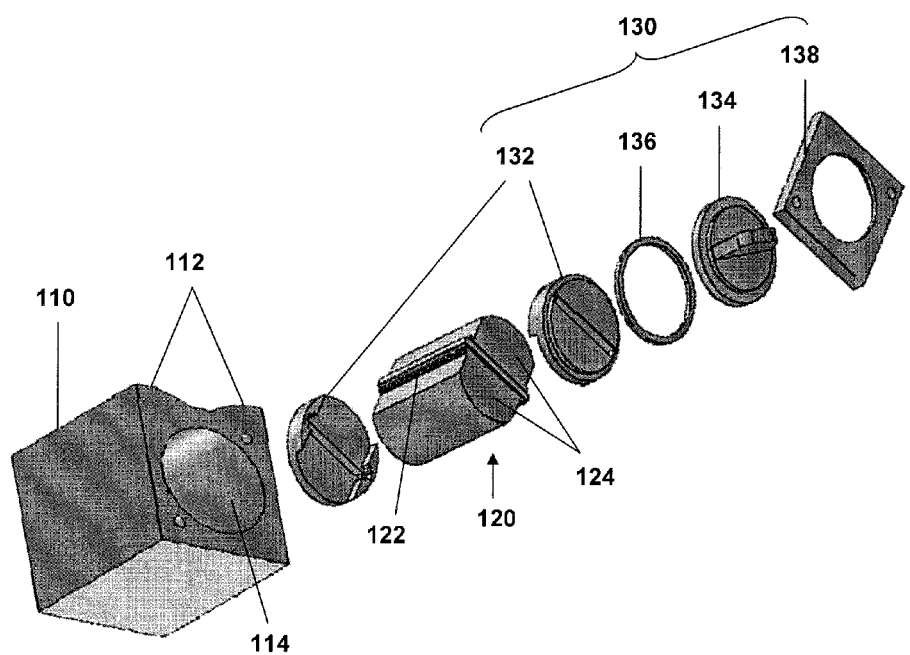
FIG. 3 is an exploded view of the coupling device including a magnet assembly, a housing, and a controlling means.

FIG. 3 shows the exploded view of the coupling device (100) in accordance to the present invention. The housing (110) may be in a rectangular shape with the cavity (114) formed in the front center of the housing (110) to receive the magnet assembly (120). However, the shape of the housing (110) is not limited to a rectangular shape but may be any shape that is fixable to the cup-shaped component (200) of the residual limb socket (20). The housing (110) has a protrusion (112) on top of the housing (110) for intensifying the magnetic field created by the magnet assembly (120). Preferably, there are two protrusions (112) on opposing sides of the housing (110) for more secure contact with the mounting plate (140).

The controlling means (130) comprises the pair of covers (132), the knob (134), the washer (136), and the frame (138). The pair of covers (132) is affixed to the magnet assembly (120) to facilitate the rotation of the magnet assembly (120) in the cavity (114) of the housing (110). The pair of covers (132) may be made of plastic material. The knob (134) is attached to one of the covers (132) at the outer end of the magnet assembly (120) for controlling the rotation of the magnet assembly (120). The frame (138) is coupled to the knob (134) and fastened to the housing (110) to position the knob (134). Optionally, the controlling means (130) may be in a form of a push button and the like, not limited to the rotating type as described in the preferred embodiment.

Figures 4A, 4B:
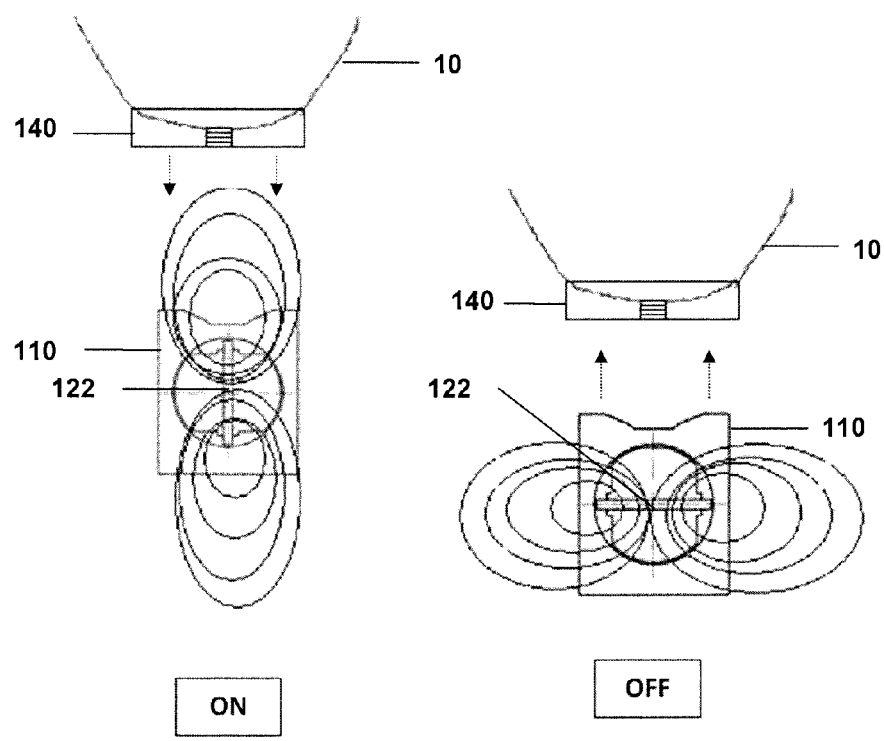
FIG. 4a illustrates a magnetic field created by the magnet assembly when the permanent magnet is vertically aligned, resulting an attraction of the mounting plate to the housing.
FIG. 4b illustrates a magnetic field created by the magnet assembly when the permanent magnet is horizontally aligned, resulting a repellent of the mounting plate from the housing.

FIG. 4a and FIG. 4b illustrate the magnetic field created by the magnet assembly (120). As seen in FIG. 4a, the mounting plate (140) is attracted to the protrusion (112) of the housing (110) when the permanent magnet (122) is vertically aligned. The magnetic field created by the magnet assembly (120) attracts the mounting plate (140) coupled to the distal end of the residual limb liner (10) towards the housing (110) placed within the distal end of the residual limb socket (20), thereby attaching the residual limb liner (10) to the residual limb socket (20). Therefore, the residual limb liner (10) is connected to the residual limb socket (20) via the coupling device (100).

As seen in FIG. 4b, the mounting plate (140) is repelled from the protrusion (112) of the housing (110) when the permanent magnet (122) is horizontally aligned. The magnetic field created by the magnet assembly (120) repels the mounting plate (140) coupled to the distal end of the residual limb liner (10) away from the housing (110) placed within the distal end of the residual limb socket (20), thereby detaching the residual limb liner (10) from the residual limb socket (20). Therefore, the residual limb liner (10) is disconnected from the residual limb socket (20) by the coupling device (100).

Said coupling device (100) is able to sustain a pulling force of a minimum of 350N. The locking mechanism of the conventional limb prosthesis has been eliminated by the use of said coupling device (100), thus, increase the durability of the limb prosthesis.

Although the present invention has been described with reference to specific embodiments, also shown in the appended figures, it will be apparent for those skilled in the art that many variations and modifications can be done within the scope of the invention as described in the specification and defined in the following claims.

Description of the reference numerals used in the accompanying drawings according to the present invention:

| Reference Numerals | Description |
| --- | --- |
| 10 | Residual limb liner |
| 20 | Residual limb socket |
| 40 | Pylon |
| 100 | Coupling device |
| 110 | Housing |
| 112 | Protrusion of housing |
| 114 | Cavity of housing |
| 120 | Magnet assembly |
| 122 | Permanent magnet |
| 124 | Pair of iron bars |
| 130 | Controlling means |
| 132 | Pair of covers |
| 134 | Knob |
| 136 | Washer |
| 138 | Frame |
| 140 | Mounting plate |
| 142 | Male connector |
| 200 | Cup-shaped component |

We claim:

1. A coupling device (100) for connecting a residual limb liner (10) to a residual limb socket (20) of a limb prosthesis, wherein:
   a magnet assembly (120) comprising a permanent magnet (122) sandwiched by a pair of solid iron bars (124) for creating a magnetic field;
   a housing (110) comprising a protrusion (112) for intensifying magnetic field and a cavity (114) for receiving the magnet assembly (120), wherein said housing (110) is embedded at a distal end of the residual limb socket (20);
   a controlling means (130) coupled to the housing (110) and the magnet assembly (120) for controlling the magnetic field by rotating the magnet assembly (120); and
   a mounting plate (140) coupled to the residual limb liner (10);
   wherein the mounting plate (140) is attracted to the protrusion (112) of the housing (110) when the permanent magnet (122) is vertically aligned, thereby attaching the residual limb liner (10) to the residual limb socket (20); and
   wherein the mounting plate (140) is repelled from the protrusion (112) of the housing (110) when the permanent magnet (122) is horizontally aligned, thereby detaching the residual limb liner (10) from the residual limb socket (20).

2. A coupling device (100) for connecting a residual limb liner (10) to a residual limb socket (20) of a limb prosthesis according to claim 1, wherein the controlling means (130) comprises: a pair of covers (132) coupled to two ends of the magnet assembly (120) to facilitate the rotation of the magnet assembly (120), a knob (134) attached to one of the covers (132) at an outer end of the magnet assembly (120), with a washer (136) placed there between, for controlling the rotation of the magnet assembly (120), and a frame (138) coupled to the knob (134) and fastened to the housing (110) to locate the knob (134).

3. A coupling device (100) for connecting a residual limb liner (10) to a residual limb socket (20) of a limb prosthesis according to claim 1, wherein the housing (110) is mounted on a pylon (40) of a limb prosthesis by fastening means.

4. A coupling device (100) for connecting a residual limb liner (10) to a residual limb socket (20) of a limb prosthesis according to claim 1, wherein the mounting plate (140) is made of stainless steel.

5. A coupling device (100) for connecting a residual limb liner (10) to a residual limb socket (20) of a limb prosthesis according to claim 1, wherein the mounting plate (140) has a flat surface for distributing the magnetic field evenly on said plate (140).

6. A coupling device (100) for connecting a residual limb liner (10) to a residual limb socket (20) of a limb prosthesis according to claim 1, wherein the mounting plate (140) is provided with a male connector (142) adapted to be received in a female connector located on a distal end of the residual limb liner (10), for fastening the mounting plate (140) to the residual limb liner (10).

* * * * *